United States Patent [19]

Suzuki et al.

[11] 4,281,064

[45] Jul. 28, 1981

[54] PROCESS FOR PRODUCING LIPIDS HAVING A HIGH LINOLEIC ACID CONTENT

[75] Inventors: Osamu Suzuki; Yoshifumi Jigami; Satoshi Nakasato; Tetsutaro Hashimoto, all of Yatabe, Japan

[73] Assignee: The Agency of Industrial Science and Technology, Tokyo, Japan

[21] Appl. No.: 107,869

[22] Filed: Dec. 28, 1979

[30] Foreign Application Priority Data

Feb. 19, 1979 [JP] Japan .................................. 54-18228

[51] Int. Cl.$^3$ ................................................ C12P 7/64
[52] U.S. Cl. ..................................... 435/134; 435/136; 435/171; 435/252; 435/254
[58] Field of Search ............... 435/135, 134, 171, 252, 435/254, 136

[56] References Cited

U.S. PATENT DOCUMENTS 2,346,011   4/1944   Damm .................................. 435/134

OTHER PUBLICATIONS

Shaw, "Fatty Acids of Fruiting Bodies of Basidiomycetes" Nature, vol. 213 (1967), pp. 86–87.
Hughes, "Mushroom Science", vol. 5 (1962), pp. 540–546.
Shulman et al., "Comparative Study of the Content of Fatty Acids & Lipids in Fungi", Chemical Abstracts, vol. 88 (1978), Abstract No. 47300e.
Bhatia et al., "Fungal Lipids", Chemical Abstracts, vol. 78, (1973), Abstract No. 24564y.
Brennan et al., Progress in the Chemistry of Fats and Other Lipids, pp. 49, 55, 56, 85, 86.
Wassef, Momtaz K., Advances of the Lipid Research, pp. 150, 178, 179, 226, 227 (1978).

*Primary Examiner*—R. B. Penland

[57] ABSTRACT

A process for producing lipids having a high linoleic acid content is provided, wherein fungi of Pellicularia genus are cultivated in a medium of a carbohydrate or vegetable fiber as a carbon source. By separating the fungus body from the resulting culture and subjecting it to solvent extraction, the objective lipid is obtained.

2 Claims, No Drawings

PROCESS FOR PRODUCING LIPIDS HAVING A HIGH LINOLEIC ACID CONTENT

BACKGROUND OF THE INVENTION

This invention relates to a process for producing lipids having a high linoleic acid content and more particularly relates to a process wherein fungi of Pellicularia genus are cultivated in a medium of a carbohydrate or vegetable fiber as a carbon source, and lipids (neutral lipids such as oil and fat and polar lipids such as phospholipid and glycolipid) having a high linoleic acid content are produced from the culture obtained by the above cultivation.

As for microorganisms yielding lipids having a high linoleic acid content reported so far, it has been known that there are those belonging to Amanita genus, Tricholoma genus and Clitocybe genus, and these polar lipid yields of which the contents of linoleic acid are 67%, 69% and 70%, respectively (R. Shaw, Nature, Lond. 213, 86~87 (1967)). Further, it has also been found that a fungus belonging to the Agaricus genus yields lipids containing 63~74% of linoleic acid (D. H. Hughes, Mushroom Sci., 5, pp. 540~546 (1962)). However, materials used as a carbon source in the case where these fungi are employed, have been limited to saccharides. Further, according to these conventional processes the content of linoleic acid in the resulting lipids has barely amounted to 70% at the highest and has been generally low; hence it has not as yet been satisfactory.

SUMMARY OF THE INVENTION

The inventors of this invention have made various studies in order to overcome the above-mentioned drawbacks and as a result have discovered that fungi of Pellicularia genus belonging to molds, yield lipids having a high linoleic acid content in a medium of either carbohydrates or vegetable fibers as a carbon source, and have completed this invention based on this discovery.

A first object of the present invention is to provide a process for producing lipids having a high linoleic acid content by cultivating fungi of the Pellicularia genus.

Another object of the present invention is to provide a process for producing lipids having a high linoleic acid content by cultivating fungi according to which not only carbohydrates but also vegetable fibers can be utilized.

Other and further objects, features and advantages of the present invention will be more fully apparent from the description mentioned below.

The present invention resides in:

A process for producing lipids, comprising cultivating a fungus of Pellicularia genus in a medium containing as a carbon source, at least one member selected from the group consisting of carbohydrates and vegetable fibers and obtaining from the resulting culture, lipids having a high linoleic acid content.

DETAILED DESCRIPTION OF THE INVENTION

As for the fungi of Pellicularia genus employed in the present invention, molds such as *Pellicularia fillamentosa* IFO 6476, 6523, 6675, 8985, 5879, 6262 and 6295, *Pellicularia praticola* IFO 6253, etc. are included, but the abovementioned fungi are not limited to these examples, but any fungi of the Pellicularia genus can be employed.

Moreover any of the fungi exemplified above are known molds which have been preserved at the Japanese Foundation, Institute for Fermentation, Osaka and recited in the IFO catalogue (list of cultures).

As for the carbohydrates as a carbon source for the medium employed for cultivating the above-mentioned molds, for example, glucose, sucrose, starch, molasses, etc. are included.

As for the vegetable fibers therefor, for example, linter pulp, wood pulp, bagasse, etc. are included.

The carbon sources are preferably used in an amount of 20–80 g/l medium. Further, as for a nitrogen source, for example, inorganic nitrogen sources such as $NH_4NO_3$ and $(NH_4)_2SO_4$ and organic nitrogen sources such as urea, peptone, yeast extract, corn steep liquor, etc. are used. As for inorganic salts, for example, $KH_2PO_4$, $K_2HPO_4$, $NaCl$, $FeSO_4.7H_2O$, $MgSO_4.7H_2O$, $ZnSO_4.7H_2O$, etc. are used. Further, trace elements and other nutritive sources are added in accordance with specific requirements. The amount of these nitrogen sources added has no particular limitation, but it is usually in the range of 1/5 to 1/100 of the amount of carbon sources. The amount of inorganic salts added can be very small. In case tap water, which usually contains such inorganic salts, is used, the addition of the salts can be omitted.

The cultivation of the above-mentioned molds is carried out under aerobic conditions and usually by stationary cultivation, shaking cultivation, aeration agitation cultivation, etc., in a liquid medium. The pH of the medium is preferably in the range of 4.0 to 6.0, and cultivation is carried out usually at 15°~38° C. for about 7~30 days.

Depending on the amount of strains of fungi of Pellicularia genus inoculated in a medium, the time when the growing strains are saturated in the medium is somewhat varied but the difference is negligible and the amount of fungi propagated, and which has reached ultimate saturation, is unchanged.

Thus, since lipids having a high linoleic acid content are produced in the culture, the lipids are collected from the culture, and since they are contained in the fungus bodies of the molds, it is preferable to separate the fungus bodies from the culture and collect lipids from the fungus bodies. The collection of lipids can be carried out according to a conventional manner, such as by solvent extraction.

Thus, according to the present invention, it is possible to obtain lipid having a high linoleic acid content (65~79%) employing carbohydrates or vegetable fibers as a carbon source. The fact that lipids having a high linoleic acid content can be produced by assimilating not only carbohydrates, but also vegetable fibers, as mentioned above, and hence, carbon sources in such a very wide range can be utilized, is an effectiveness which has been utterly unexpected from conventional fungi. The lipids obtained according to the process of the present invention are neutral lipids (such as oil and fat), polar lipids (phospholipid ad glucolipid), etc. These lipids having a high linoleic acid content, e.g. oil and fat, are edible in the form of salad oil, etc., in place of current materials collected from safflower oil, etc. Further, they can also be used as industrial raw materials such as those for dimeric acids as well as for fatty acid derivatives (see Suzuki et al, Yukagaku (Journal of Japan Oil chemists' Society), 27, 76 (1978)).

The present invention will be more clearly understood with referrence to the following Examples:

EXAMPLE 1

A medium was prepared by mixing 30 g of glucose 3 g of $NH_4NO_3$, 3 g of $KH_2PO_4$, 0.3 g of $MgSO_4.7H_2O$, S0.2 g of malt extract, 0.2 g of yeast extract, 10 mg of $FeSO_4.7H_2O$, 1.2 mg of $CaCl_2.2H_2O$, 0.2 mg of $CuSO_4.5H_2O$, and 1.0 Omg of $ZnSO_4.7H_2O$ (1.0 mg) together in 1000 ml of deionized water. Then the pH of medium was adjusted to 4.6. Two hundred ml of the resulting medium were placed in a 500 ml Erlenmeyer flask. The respective strains shown in Table 1 were inoculated in the medium prepared above in an inoculation amount of one platinum loop and stationary cultivation was carried out at a set temperature and for a set period.

After cultination, fungus bodies were collected by filtration or centrifugation. A portion of the fungus bodies was precisely weighed and dried in a constant temperature bath at 120° C. for 24 hours to measure their water content. The remaining portion of the fungus bodies was subjected to extraction of lipids. In this extraction, a mixed liquid of chloroform-methanol (2:1 v/v) was added to the remaining portion of the wet fungus bodies and the resulting mixture was homogenized in the presence of glass beads, whereby milling of the fungus bodies and extraction of lipids were carried out at the same time. For complete extraction, both the milling and extraction steps were repeated 5 timees, and the resulting extracted liquids were collected together and purified according to Floch's partition washing method followed by distilling off of the solvents under reduced pressure and measuring the total amount of lipids according to a weight method.

From the lipids extracted from the fungus bodies and precisely weighed, a part was taken and subjected to methyl esterification, followed by analyzing the composition of fatty acids by gas chromatography. The remainder of the lipids was subjected to a column chromatography employing Unisil (Tradename, manufactured by Clarkson Chemical Company, Inc.) as filler and chloroform and methanol as the developing solvent, to separate neutral lipids and polar lipids therefrom, whereby the respective amounts present were observed. At the same time, respective lipids were also subjected to gas chromatography to observe the composition of fatty acids. The results as to the Pellicularia genus molds, obtained by such a method, are shown in Table 1 together with cultivation conditions. In addition, these results were shown under calculation in terms of per 200 ml of medium.

From Table 1, it is observed that the amount of lipids formed and the content of lipids vary depending on the difference of strains, but as for the fatty acid composition of lipids, it is seen that the content of linoleic acid is high in any case.

TABLE 1

| Name of strain | IFO No. | Cultivation day | Temperature (°C.) | Amount of fungus bodies formed DC (g) | Total amount of lipids formed (TL) (mg) | TL/DC (%) | Neutral lipids (NL) NL/DC (%) | Polar lipids (PL) PL/DC (%) | (in 200 ml of medium) Linoleic acid content |  |  |
|---|---|---|---|---|---|---|---|---|---|---|---|
|  |  |  |  |  |  |  |  |  | TL (%) | NL (%) | PL (%) |
| Pellicularia fillametosa | 6476 | 30 | 30 | 0.6792 | 60.4 | 8.9 | 5.8 | 3.1 | 75.0 | 71.4 | 83.4 |
|  | 6523 | 29 | 30 | 0.6442 | 41.0 | 6.4 | 4.1 | 2.3 | 71.9 | 70.9 | 77.3 |
| f. sp. sasakii | 6675 | 14 | 30 | 1.3844 | 167.8 | 12.1 | 9.8 | 2.3 | 68.2 | 62.6 | 80.6 |
| f. sp. sasakii | 8985 | 14 | 30 | 2.1002 | 119.3 | 5.7 | 4.2 | 1.5 | 67.9 | 63.9 | 80.0 |
| f. sp. sasakii | " | 25 | 20 | 0.9619 | 68.3 | 7.1 | 7.1 | 5.4 | 74.7 | 70.1 | 87.2 |
| f. sp. solanii | 5879 | 21 | 30 | 0.6388 | 129.5 | 20.3 | 14.4 | 5.9 | 76.2 | 72.2 | 80.6 |
| f. sp. solanii | " | 34 | 20 | 0.6046 | 64.1 | 10.6 | 8.0 | 2.6 | 76.5 | 70.1 | 78.9 |
| f. sp. solanii | 6262 | 14 | 30 | 0.6495 | 97.7 | 15.0 | 11.5 | 3.5 | 73.2 | 66.0 | 83.9 |
| f. sp. timsii | 6295 | 30 | 30 | 0.5144 | 33.4 | 6.5 | 3.9 | 2.6 | 75.0 | 67.4 | 76.2 |
| Pellicularia praticola | 6253 | 24 | 30 | 0.5409 | 168.8 | 31.2 | 25.5 | 5.7 | 78.6 | 72.4 | 82.9 |
|  | " | 30 | 20 | 1.4478 | 105.8 | 7.3 | 3.7 | 3.6 | 75.7 | 67.5 | 79.6 |

EXAMPLE 2

A medium was prepared by mixing 30 g of glucose or powdery cellulose (Avicel,(Tradename) manufactured by Merck Ltd.), 3 g of $KH_2PO_4$, 3 g of $NH_4NO_3$, 0.5 g of $MgSO_4.7H_2O$, 0.1 g of Nacl, 10 mg of $FeSO_4.7H_2O$, 10 mg of $CaCl_2.2H_2O$, 0.2 mg of $CuSO_4.5H_2O$, 1.0 mg of $ZnSO_4.7H_2O$, 1.0 mg of $MnCl_2.4H_2O$, 2 mg of Thiamine-HCl and 0.02 mg of D-Biotin together in 1000 ml of deionized water, the pH of which was then adjusted to 4.6. Two hundred ml of the medium thus prepared was placed in a 500 ml Erlenmeyer flask. The respective strains shown in Table 1 were inoculated in the medium prepared above in an inoculation amount of one platinum loop, and shaking cultivation was carried out at 150 rpm at a set temperature and for a set period. After cultivation, extraction and separation of lipids were carried out in the same manner as in Example 1 to observe their fatty acid compositions. Cultivation conditions and results are shown in Table 2.

From the results of Table 2, it is observed that even in the case of using cellulose as a carbon source, the growth of the Pellicularia genus molds is good and a considerable amount of lipids is formed. Further, as for the amount of lipids formed, it was observed that the amount was considerably varied depending on the difference in the cultivation conditions such as the differences in the strain and the carbon source, but it is seen that in the case of shaking cultivation, too, the amount of fungus bodies formed is large and the linoleic acid content is high not only in the case of using glucose as a carbon source, but also in the case of using cellulose.

Moreover, when cellulose was used as a carbon source, the amount of fungus bodies formed was not persued correctly since cellulose somewhat remained; hence the content of lipids was also not known.

Having described specific embodiments of our invention, it is obvious that modifications and variations of our invention are possible in light of the above teachings.

What is claimed is:

1. A process for producing lipids comprising the steps of:
  (a) cultivating a fungus of the Pellicularia genus aerobically in a liquid containing 20–80 g/l of a carbon source selected from the group consisting of glucose, sucrose, starch, molasses, and cellulose, a nitrogen source in the range of 1/5 to 1/100 of the amount of carbon sources, and an inorganic salt; and
  (b) separating lipids having a high linoleic acid content from the resulting culture.

2. A process according to claim 1, wherein said separating step includes separating fungus bodies from said medium, milling the fungus bodies and extracting lipid from the milled fungus bodies with an organic solvent.

TABLE 2

| Name of strain | IFO No. | Carbon source | Cultivation day | Temperature (°C.) | Amount of fungus bodies formed DC (g) | Total amount of lipids formed (TL) (mg) | Total amount of lipids formed (TL) TL/DC (%) | Neutral lipids (NL) NL/DC (%) | Polar lipids (PL) PL/DC (%) | Linoleic acid content TL (%) |
|---|---|---|---|---|---|---|---|---|---|---|
| Pellicularia fillamentosa | 6675 | G | 10 | 20 | 1.1344 | 62.8 | 5.5 | 3.5 | 2.0 | 71.9 |
| f. sp. sasakii | 8985 | G | 10 | 20 | 0.9163 | 52.8 | 5.8 | 3.0 | 2.8 | 78.9 |
| f. sp. sasakii | " | G | 10 | 30 | 1.0497 | 189.1 | 18.0 | 12.7 | 5.3 | 67.8 |
| f. sp. sasakii | " | C | 10 | 30 | | 71.4 | | | | 74.1 |
| f. sp. solanii | 5879 | G | 10 | 20 | 1.8330 | 114.0 | 6.2 | 4.0 | 2.2 | 74.1 |
| f. sp. solanii | " | G | 30 | 20 | 1.5845 | 62.6 | 4.0 | 1.8 | 2.2 | 79.3 |
| f. sp. solanii | " | G | 10 | 30 | 0.9115 | 139.8 | 15.3 | 9.4 | 5.9 | 74.9 |
| f. sp. solanii | " | C | 10 | 20 | | 56.1 | | | | 71.8 |
| f. sp. solanii | " | C | 30 | 20 | | 47.6 | | | | 76.5 |
| f. sp. solanii | " | C | 10 | 30 | | 68.7 | | | | 76.3 |
| f. sp. solanii | 6262 | G | 10 | 20 | 0.9299 | 95.9 | 10.3 | 7.4 | 2.9 | 69.8 |
| f. sp. timsii | 6295 | G | 10 | 20 | 0.6917 | 200.8 | 29.0 | 23.8 | 5.2 | 65.7 |
| Pellicularia praticola | 6253 | G | 10 | 20 | 1.0220 | 59.2 | 5.8 | 3.5 | 2.3 | 68.3 |
| | " | G | 30 | 20 | 0.9317 | 47.4 | 5.1 | 2.9 | 2.2 | 76.1 |
| | " | G | 10 | 30 | 1.1433 | 69.2 | 6.1 | 3.0 | 3.1 | 76.2 |
| | " | C | 10 | 30 | | 48.8 | | | | 65.2 |

Note
G: Glucose
C: Cellulose